United States Patent
Okoshi et al.

(12)
(10) Patent No.: US 6,458,994 B2
(45) Date of Patent: Oct. 1, 2002

(54) PROCESS FOR PRODUCING AROMATIC POLYCARBOXYLIC ACID

(75) Inventors: Atsushi Okoshi; Etsuo Urabe; Masashi Yabuno; Hiroshi Ogawa; Kazuo Tanaka, all of Kurashiki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 09/861,629

(22) Filed: May 22, 2001

(30) Foreign Application Priority Data

Jun. 27, 2000 (JP) ......................... 2000-192472

(51) Int. Cl.⁷ ..................... C07C 51/16; C07C 51/255
(52) U.S. Cl. ..................... 562/416; 562/408; 562/409
(58) Field of Search .............................. 562/408, 409, 562/416

(56) References Cited

U.S. PATENT DOCUMENTS

| 4,346,232 A | * | 8/1982 | Komatsu et al. | ............ 562/416 |
| 4,755,622 A | * | 7/1988 | Schammel et al. | ......... 562/413 |
| 4,816,601 A | | 3/1989 | Lowry et al. | ................ 562/413 |
| 4,824,992 A | | 4/1989 | Tanaka et al. | ............... 562/416 |

FOREIGN PATENT DOCUMENTS

| JP | 7-116097 | 12/1995 |
| JP | 2939346 | 6/1999 |

* cited by examiner

*Primary Examiner*—Paul J. Killos
*Assistant Examiner*—Zachary Tucker
(74) *Attorney, Agent, or Firm*—Armstrong, Westerman & Hattori, LLP

(57) ABSTRACT

A process for producing a polycarboxylic acid which comprises performing liquid phase oxidation of polyalkyl-substituted aromatic aldehyde and/or oxide derivative of polyalkyl-substituted aromatic aldehyde as raw material for oxidation with molecular oxygen at two stages in water solvent in the presence of a catalyst comprising bromine or both bromine and a heavy metal(s) at a temperature of 180 to 280 ° C., thereby producing trimellitic acid or pyromellitic acid, wherein said liquid phase oxidation is performed in a continuous operation at the first stage and in a continuous operation or in a batch operation at the second stage and a total amount of bromine in said catalyst is divided to add separately at each the first stage and the second stage.

8 Claims, No Drawings

PROCESS FOR PRODUCING AROMATIC POLYCARBOXYLIC ACID

BACKGROUND OF THE INVENTION

1. Field of the Invention

The present invention relates to a process for producing an aromatic polycarboxylic acid by liquid phase oxidation of polyalkyl-substituted aromatic aldehyde and/or oxide derivative thereof, and specifically, to process for producing trimellitic acid or pyromellitic acid.

2. Prior Art

As industrial processes for producing trimellitic acid, a process comprising air-oxidizing psuedocumene as a raw material in an acetic acid solvent in the presence of a cobalt-manganese-bromine catalyst and a process comprising air-oxidizing 2,4-dimethyl benzaldehyde, 2,5-dimethyl benzaldehyde and 3,4-dimethyl benzaldehyde or 2,4-dimethyl benzoic acid, 2,5-dimethyl benzoic acid and 3,4-dimethyl benzoic acid of oxide derivative thereof as raw materials in water solvent in the presence of a catalyst containing bromine and manganese or cerium are widely known. As industrial processes for producing pyromellitic acid, a process comprising air-oxidizing durene as a raw material in an acetic acid solvent in the presence of a cobalt-manganese-bromine catalyst and a process comprising air-oxidizing 2,4,5-trimethyl benzaldehyde or 2,4,5-trimethyl benzoic acid of an oxide derivative thereof as a raw material in water solvent in the presence of a bromine-manganese-iron catalyst are known.

Among above-mentioned known processes, regarding the process comprising air-oxidizing psuedocumene in an acetic acid solvent, a production art of aromatic dicarboxylic acid, e.g., terephthalic acid has been applied to oxidation of psuedocumene. The reaction in the production of terephthalic acid is comparatively readily completed, i.e., continuously and about quantitatively completed in the presence of a comparatively low concentration of catalyst and promotor. In contrast, oxidation of psuedocumene has a defect that the metal catalyst forms a salt with trimellitic acid of a product to deposit, so that activity of the catalyst is degraded and the reaction does not readily progress.

Japanese Patent No. 2939346 describes that air oxidation of psuedocumene is performed semi-continuously or in a batch wise while controlling the first stage of the reaction to a comparatively low temperature and then in a batch wise while controlling the second stage of the reaction to a comparatively high temperature and most bromine catalyst and trivalent cerium are added at the second stage to decrease contact of trimellitic acid as a product with a zirconium-cobalt-manganese-bromine catalyst and to depress degradation of catalyst activity due to formation of an insoluble salt of trimellitic acid with zirconium, cobalt and manganese, whereby the yield of trimellitic acid is improved.

Japanese Patent Publication No. 7-55917 discloses a process for producing pyromellitic acid comprising air-oxidizing durene in an acetic acid solvent in the same manner as in the above-mentioned process for producing trimellitic acid.

On the other hand, Japanese Patent Publication No. 58-2222 describes that polyalkyl-substituted aromatic aldehyde or oxide derivative thereof is oxidized with molecular oxygen in water solvent in the presence of a bromine and a metal ion catalyst selected from the group consisting of manganese and cerium while maintaining an oxygen concentration in an exhaust gas in an outlet of the reactor to 3% or above, whereby the corresponding aromatic polycarboxylic acid can be obtained readily in a high yield in one stage reaction. The process provides advantages that there is no combustion of solvent and no recovery step of solvent is required on account of water solvent and furthermore continuous reaction can be performed since no degradation of catalyst activity due to formation of a salt of the metal catalyst with trimellitic acid or pyromellitic acid of a product occurs.

Japanese Patent Publication No. 7-116097 discloses a process comprising oxidizing 2,4,5-trimethyl benzaldehyde with a molecular oxygen-containing gas in water solvent containing bromine ion, manganese ion and iron ion to depress combustion of 2,4,5-trimethyl benzaldehyde, thereby improving the yield of pyromellitic acid.

Trimellitic acid has been widely used as a raw material for alkyd resins, high grade plasticizers, polyamideimides and polyesters. Pyromellitic acid is very useful as a raw material for cross linking agents for foam polyester, particular plasticizers, polyimides and powder coating agents. In order to use trimellitic acid and pyromellitic acid as these raw materials, a high purity of product thereof is required.

The process for producing trimellitic acid disclosed in Japanese Patent No. 2939346 comprising air-oxidizing psuedocumene in an acetic acid solvent has defects that the operation is complicated since it is necessary to control carefully and change a temperature and a water concentration in the reaction liquid; a high price catalysts such as cobalt zirconium and cerium are used; there is combustion of acetic acid as solvent and a recovery equipment of acetic acid as solvent is necessary.

The process for producing pyromellitic acid disclosed in Japanese Patent Publication No.7-55917 comprising air-oxidizing durene in an acetic acid solvent is not economical from the aspects that a high price is imposed on durene of the raw material since it is difficult to obtain it and the yield of pyromellitic acid is about 60 mol% since the oxidation reaction is more difficult than that in the process for producing trimellitic acid comprising air-oxidizing psuedocumene in an acetic acid solvent.

The processes for producing trimellitic acid and pyromellitic acid disclosed in Japanese Patent Publication Nos. 58-2222 and 7-116097 comprising oxidizing polyalkyl-substituted aromatic aldehyde or oxide derivative thereof with molecular oxygen in water solvent can overcome the defects in the process used an acetic acid solvent, but it is necessary to reduce further organic bromine compounds and oxidation intermediates produced as by-products in order to obtain the intended substance in a high yield.

SUMMARY OF THE INVENTION

An object of the present invention is to provide a process for producing trimellitic acid or pyromellitic acid comprising oxidizing polycakyl-substituted aromatic aldehyde and/or oxide derivative thereof in which by-product content is small and a high yield can be obtained.

As a result of extensive studies to solve above-mentioned prior art problems, the inventors have found that polyalkyl-substituted aromatic aldehyde and/or oxide derivative thereof as raw material for oxidation is oxidized with molecular oxygen in water solvent in the presence of a catalyst containing bromine or both bromine and a heavy metal(s) at 180 to 280 °C. wherein the raw material for oxidation and the catalyst are fed to perform the reaction and then bromine in the catalyst is further added thereto to perform further the reaction, whereby the amount of organic bromine compounds and oxide intermediates to be by-produced are reduced and the yield of trimellitic acid or pyromellitic acid of intended substances is improved, and have accomplished the present invention.

That is, a process for producing a polycarboxylic acid which comprises performing liquid phase oxidation of polyalkyl-substituted aromatic aldehyde and/or oxide derivative of polyalkyl-substituted aromatic aldehyde as raw material for oxidation with molecular oxygen at two stages in water solvent in the presence of a catalyst comprising bromine or both bromine and a heavy metal(s) at a temperature of 180 to 280° C., thereby producing trimellitic acid or pyromellitic acid, wherein said liquid phase oxidation is performed in a continuous operation at the first stage and in a continuous operation or in a batch operation at the second stage and a total amount of bromine in said catalyst is divided to add separately at each the first stage and the second stage.

DETAILED DESCRIPTION OF THE INVENTION

Examples of polyalkyl-substituted aromatic aldehyde of a raw material for oxidation include 2,4-dimethyl benzaldehyde, 2,5-dimethyl benzaldehyde and 3,4-dimethyl benzaldehyde, which are used as a raw material for production of trimellitic acid. Further, 2,4,5-trimethyl benzaldehyde is used as a raw material for production of pyromellitic acid.

The above-mentioned polyalkyl-substituted aromatic aldehydes can be quantitatively obtained without by-production of isomers by reaction of polyalkylbenzene with carbon monoxide in the presence of a HF—BF$_3$ catalyst.

In the present invention, oxide derivatives of polyalkyl-substituted aromatic aldehyde also can be used as a raw material for oxidation. Examples of the oxide derivatives include 2,4-dimethyl benzoic acid, 2,5-dimethyl benzoic acid and 3,4-dimethyl benzoic as a raw material for production of trimellitic acid and 2,4,5-trimethyl benzoic acid as a raw material for production of pyromellitic acid.

As the catalyst for oxidation reaction, bromine alone can be used, but it is preferable to use both bromine and a heavy metal (s). The heavy metal is used in the form of heavy metal ion and includes various heavy metals, among which manganese, iron, cerium, nickel, chromium, molybedenum, lead, tin, cobalt and niobium are preferable, and manganese is more preferable in the production of trimellitic acid and a combination of manganese and iron is more preferable in the production of pyromellitic acid.

Examples of heavy metal ion source include manganese hydroxide, manganese acetate, manganese acetylacetonate, manganese benzoate, manganese borate, manganese carbonate, manganese bromide, manganese chloride, manganese formate, manganese iodide, manganese oxalate, iron hydroxide, iron oxide, iron acetylaceacetonate, iron bromide and iron chloride, among which bromides such as manganese bromide and iron bromide are preferable.

The bromine in the catalyst is used in the form of bromine ion. Examples of bromine ion source include any substance capable of generating bromine ion under the reaction conditions including inorganic bromides such as hydrogen bromide, ammonium bromide, sodium bromide and manganese bromide and organic bromides such as benzyl bromide and methane tetrabromide, among which hydrogen bromide, manganese bromide and iron bromide are preferable.

In the production of trimellitic acid, total amount of bromine ion in the catalyst to be added is 1 to 5% by weight and preferably 1.5 to 4% by weight to water solvent and the amount of manganese ion is 0.05 to 1% by weight and preferably 0.1 to 0.5% by weight to water solvent.

In the production of pyromellitic acid, total amount of bromine ion in the catalyst to be added is 1 to 5% by weight and preferably 1.5 to 4% by weight to water solvent and the amount of manganese ion is 0.05 to 1% by weight and preferably 0.1 to 0.5% by weight to water solvent and the amount of iron ion is 0.1 to 100 ppm and preferably 1 to 50 ppm to water solvent.

When bromine ion is below 1% by weight, combustion of polyalkyl-substituted aromatic aldehyde or oxide derivative thereof is increased, whereas above 5% by weight the reaction tends to be depressed.

It is preferable that the amount of bromine ion to be additionally fed in the reaction of the second stage is 5 to 50% by weight to total amount of bromine ion to be fed. The additional feeding of bromine ion in the above-mentioned range improves the oxidation reaction rate, and decomposes and reduces organic bromine compounds in the reaction system and reduces the amount of oxide intermediates to be produced, whereby trimellitic acid or pyromellitic acid is obtained in a high yield.

The reaction temperature at the first stage and the second stage is 180 to 280° C. and preferably 200 to 260° C. Each the reaction temperature at the first stage and the second stage can be selected in each the range. Although the reaction pressure, usually, is spontaneously decided through the process to maintain the temperature to a constant temperature by operation of vaporization of water solvent and condensation reflux, it can be also maintained to a preferable constant pressure by means of heat exchange from the outside. The range of the reaction pressure is not limited on the condition that the reaction liquid can keep the state of liquid phase, but the range of 1.5 to 6 MPa is usually applied.

The amount of water as the solvent is 2 times by weight or above and preferably 3 to 6 times by weight to the raw material. The residence time at the first stage and the second stage of the reaction is, respectively, preferably 0.2 to 3.0 hours and more preferably 0.5 to 2.0 hours.

The reaction can be performed in a continuous operation at the first stage and in a continuous operation or in a batch operation at the second stage. Particularly, in order to display the advantageous effects of the present invention, continuous two stage type oxidation process to perform the reaction in a continuous operation at both the first stage and the second stage is most preferable.

After the completion of oxidation, the reaction liquid is subjected to known purifying treatments such as filtration and distillation, whereby trimellitic acid or pyromellitic acid can be obtained as a product.

PREFERRED EMBODIMENT OF THE INVENTION

The present invention will be described in more detail below, referring to Examples and Comparative Examples, which are not intended to limit the scope of the present invention.

The organic bromine compound concentration described in Examples and Comparative Examples was converted into a bromine concentration. That is, a bromine content in an organic bromine compound, i.e., a bromine conversion concentration was determined by subtraction of a bromine ion concentration from total bromine concentration in a reaction liquid. Herein, the total bromine concentration was measured according a fluorescent X ray analysis method and the bromine ion concentration was measured according to a silver nitrate titration method.

The oxide intermediate in the production of trimellitic acid means sum total of methyl phthalic acid, 1-carboxy-3, 4-phthalide and dimethyl benzoic acid. The oxide intermediate in the production of pyromellitic acid means sum total of methyl trimellitic acid, 1,2-dicarboxy-4,5-phthalide and 2,4,5-trimethyl benzoic acid. As a criterion to exhibit a situation of production of these oxide intermediates, a production percentage calculated on the basis of raw material mol in the same manner as in the yield of intended substance was indicated.

Example 1

A catalyst liquid of bromine ion concentration 2.3% by weight and manganese ion concentration 0.39% by weight mixed 1452 g of water, 17.5 g of 100% hydrogen bromide and 30.5 g of manganese bromide (tetrahydrate) was charged to the first stage reactor in a continuous two stage type reactor, connected two zirconium autoclaves of inner capacity 2 L equipped with a reflux condenser, a stirrer, a heater, a raw material feeding port, a gas introducing port and reaction product withdrawing port and 1000 g of the catalyst liquid having the same components as in the first stage reactor was charged to the second stage reactor. Nitrogen was fed under an applied pressure via the gas introducing port to elevate the interior pressure of the first stage reactor up to 1 MPa and the interior temperature of the first and second stage reactors was elevated up to 220 ° C. with the heater. Then, each 2,4-dimethyl benzaldehyde at the rate of 200 g/hr and the catalyst liquid having the same components as in the catalyst liquid charged to each reactor at the rate of 750 g/hr was separately fed to the first stage reactor. Introduction of air via the gas introducing port was started simultaneously with feeding of 2,4-dimethyl benzaldehyde and a flow rate of air was controlled so as to maintain oxygen in the exhaust gas from the first stage reactor to 2.5%. Then, transfer of the reaction liquid from the first stage reactor to the second stage reactor was started while maintaining the liquid level in the first stage reactor to a constant liquid level and simultaneously a catalyst liquid of bromine ion concentration 3.3% by weight mixed 58 g of water and 2 g of 100% hydrogen bromide was fed to the second stage reactor at the rate of 60 g/hr and introduction of air via the gas introducing port was started and a flow rate of air was controlled so as to maintain oxygen in the exhaust gas from the second stage reactor to 4.5%. 1150 g/hr of the reaction product was withdrawn from the second stage reactor while maintaining the liquid level in the second stage reactor to a constant liquid level. Meantime, the pressure in the reactors was maintained to 3.2 MPa at the first stage and to 2.9 MPa at the second stage. The amount of bromine ion fed to the second stage occupied 10.5% of total amount of fed bromine ion. After the components in the reactor had become steady, the products were analyzed. The result was shown in Table 1.

Comparative Example 1

The oxidation of 2,4-dimethyl benzaldehyde was continuously performed in the same manner as in Example 1 except that the catalyst liquid was not fed to the second stage reactor. The result was shown in Table 1.

Comparative Example 2

One of the same autoclave as in Example 1 was used as a continuous one stage type reactor. A catalyst liquid of bromine ion concentration 2.3% by weight and manganese ion concentration 0.39% by weight mixed 1452 g of water, 17.5 g of 100% hydrogen bromide and 30.5 g of manganese bromide (tetrahydrate) was charged to the reactor. Nitrogen was fed under an applied pressure via the gas introducing port to elevate the interior pressure of the reactor to 1 MPa and the interior temperature of the reactor was elevated up to 220° C. with the heater. Then, each 2,4-dimethyl benzaldehyde at the rate of 100 g/hr and the catalyst liquid having the same components as in the catalyst liquid charged to the reactor at the rate of 375 g/hr was separately fed to the reactor. Introduction of air via the gas introducing port was started simultaneously with feeding of 2,4-dimethyl benzaldehyde and a flow rate of air was controlled so as to maintain oxygen in the exhaust gas from the reactor to 2.5%. The reaction product was withdrawn so as to maintain the liquid level in the reactor to a constant liquid level. Meantime, the pressure in the reactor was maintained to 3.2 MPa. The result was shown in Table 1.

Example 2

The oxidation of 2,4-dimethyl benzaldehyde was continuously performed in the same manner as in Example 1 except that the catalyst liquid to be charged to each reactor and to be fed to the first stage reactor was changed to a catalyst liquid of hydrogen bromide concentration 1.4% by weight and manganese ion concentration 0.39% by weight mixed 1465.5 g of water, 4.0 g of 100% hydrogen bromide and 30.5 g of manganese bromide (tetrahydrate) and the amount of the catalyst liquid to be fed to the second stage reactor was changed to 90 g/hr. The amount of bromine ion fed to the second stage occupied 22.2% of total amount of fed bromine ion. The result was shown in Table 1.

Example 3

The oxidation of 2,4-dimethyl benzaldehyde was continuously performed in the same manner as in Example 1 except that the catalyst liquid to be charged to each reactor and to be fed to the first stage reactor was changed to a catalyst liquid of hydrogen bromide concentration 2.0% by weight and manganese ion concentration 0.39% by weight mixed 1456.5 g of water, 13.0 g of 100% hydrogen bromide and 30.5 g of manganese bromide (tetrahydrate) and the amount of the catalyst liquid to be fed to the second stage reactor was changed to 120 g/hr. The amount of bromine ion fed to the second stage occupied 21.1 % of total amount of fed bromine ion. The result was shown in Table 1.

Example 4

The oxidation was continuously performed in the same manner as in Example 1 except that 2,4-dimethyl benzaldehyde was changed to 2,4,5-trimethyl benzaldehyde and the catalyst liquid to be charged to each reactor and to be fed to the first stage reactor was changed to a catalyst liquid of bromine ion concentration 2.3% by weight, manganese ion concentration 0.44% by weight and iron ion concentration 13 ppm mixed 1450.3 g of water, 15.3 g of 100% hydrogen bromide, 34.4 g of manganese bromide (tetrahydrate) and 0.1 g of ferric bromide and the amount of the catalyst liquid to be fed to the first stage reactor was changed to 780 g/hr and 2,4,5-trimethyl benzaldehyde was fed at the rate of 90 g/hr. The amount of bromine ion fed to the second stage occupied 10.0 % of total amount of fed bromine ion. The yield of pyromellitic acid was 82.4%. The bromine conversion concentration of organic bromine compound was 0.07%. The production percentage of oxide intermediate was 2.5%.

Comparative Example 3

The oxidation of 2,4,5-trimethyl benzaldehyde was continuously performed in the same manner as in Example 4 except that the catalyst liquid was not fed to the second stage reactor. The yield of pyromellitic acid was 80.1%. The bromine conversion concentration of organic bromine compound was 0.24%. The production percentage of oxide intermediate was 3.2%

Example 5

The oxidation was continuously performed in the same manner as in Example 1 except that 2,4-dimethyl benzaldehyde was changed to 2,4-dimethyl benzoic acid and 2,4-dimethyl benzoic acid was fed at the rate of 225 g/hr. The amount of bromine ion fed to the second stage occupied 10.5% of total amount of fed bromine ion. The yield of trimellitic acid was 92.3%. The bromine conversion concentration of organic bromine compound was 0.12%. The production percentage of oxide intermediate was 0.6%.

As clear from Examples, liquid phase oxidation of polyalkyl-substituted aromatic aldehyde or oxide derivative thereof was performed in a continuous operation in water solvent and bromine ion was additionally fed according to the process of the present invention, whereby the amount of organic bromine compound and oxide intermediate to be by-produced in the reaction liquid was reduced and the yield of aromatic polycarboxylic acid was increased.

The process of the present invention is industrially very excellent since liquid phase oxidation is performed in a continuous operation in water solvent. Thus, industrial significance of the present invention is large.

TABLE 1

| Example & Comparative Ex. | Example 1 | Comp. Ex. 1 | Comp. Ex. 2 | Example 2 | Example 3 |
| --- | --- | --- | --- | --- | --- |
| Reactor | 2 stages | 2 stages | 1 stage | 2 stages | 2 stages |
| Amount of catalyst liquid fed to second stage reactor (g/hr) | 60 | 0 | — | 90 | 120 |
| Organic bromine compound in reaction liquid (bromine conversion concentration %) | 0.20 | 0.40 | 0.45 | 0.15 | 0.22 |
| Yield of trimellitic acid (%) | 92.0 | 89.5 | 87.5 | 92.2 | 92.1 |
| Production percentage of oxide intermediate (%) | 1.0 | 1.9 | 3.3 | 0.8 | 1.3 |

What is claimed is:

1. A process for producing a polycarboxylic acid which comprises performing liquid phase oxidation of polyalkyl-substituted aromatic aldehyde and/or oxide derivative of polyalkyl-substituted aromatic aldehyde as raw material for oxidation with molecular oxygen at two stages in water solvent in the presence of a catalyst comprising bromine at a temperature of 180 to 280° C. thereby producing trimellitic acid or pyromellitic acid, wherein said liquid phase oxidation is performed in a continuous operation at the first stage and in a continuous operation or in a batch operation at the second stage and a total amount of bromine in said catalyst is divided to add separately at each the first stage and the second stage.

2. The process according to claim 1, wherein an amount of bromine to be added at the second stage is 5 to 50% by weight of total amount of bromine.

3. The process according to claim 1, wherein said polyalkyl-substituted aromatic aldehyde and/or oxide derivative of polyalkyl-substituted aromatic aldehyde as raw material for oxidation is (are) 2,4-dimethyl benzaldehyde, 2,5-dimethyl benzaldehyde, 3,4-dimethyl benzaldehyde, 2,4-dimethyl benzoic acid, 2,5-dimethyl benzoic acid and/or 3,4-dimethyl benzoic acid and trimellitic acid is produced.

4. The process according to claim 3, wherein a bromine ion concentration in said water solvent is 1 to 5% by weight and a manganese ion concentration in said water solvent is 0.05 to 1% by weight.

5. The process according to claim 1, wherein said polyalkyl-substituted aromatic aldehyde and/or oxide derivative of polyalkyl-substituted aromatic aldehyde as raw material for oxidation is (are) 2,4,5-trimethyl benzaldehyde and/or 2,4,5-trimethyl benzoic acid and pyromellitic acid is produced.

6. The process according to claim 5, wherein a bromine ion concentration in said water solvent is 1 to 5% by weight and a manganese ion concentration in said water solvent is 0.05 to 1% by weight and an iron ion concentration in said water solvent is 0.1 to 100 ppm.

7. The process of claim 1, said catalyst further comprising a heavy metal (s).

8. The process of claim 7, said catalyst comprising hydrogen bromide and manganese bromide.

* * * * *